(12) United States Patent
Hessel et al.

(10) Patent No.: US 6,726,660 B2
(45) Date of Patent: Apr. 27, 2004

(54) IMPLANT

(75) Inventors: Lassel L Hessel, Svendborg (DK); Jepser Malling, Svendborg (DK)

(73) Assignee: Biotap A/S, Svendborg (DK)

( * ) Notice: Subject to any disclaimer, the term of this patent is extended or adjusted under 35 U.S.C. 154(b) by 0 days.

(21) Appl. No.: 10/047,306

(22) Filed: Jan. 14, 2002

(65) Prior Publication Data

US 2002/0099344 A1 Jul. 25, 2002

Related U.S. Application Data (63) Continuation of application No. PCT/DK00/00394, filed on Jul. 12, 2000.

(30) Foreign Application Priority Data

Jul. 15, 1999 (DK) .......................................... 1999 01026
Mar. 28, 2000 (DK) .......................................... 2000 00521

(51) Int. Cl.[7] .......................... A61M 5/32; A61F 5/44; A61F 2/04
(52) U.S. Cl. ..................... 604/175; 604/338; 623/23.64
(58) Field of Search ................ 604/338, 327, 604/343, 331, 332, 337, 339, 341, 342, 317, 175, 93.01, 533, 534, 538, 539; 623/11.11, 23.64, 23.65, 23.66, 23.69

(56) References Cited

U.S. PATENT DOCUMENTS

| | | | | |
|---|---|---|---|---|
| 2,154,202 A | * | 4/1939 | Gricks | |
| 2,790,442 A | * | 4/1957 | Donaldson | |
| 3,216,420 A | | 11/1965 | Smith et al. | 128/283 |
| 4,183,357 A | | 1/1980 | Bentley et al. | 128/283 |
| 4,217,664 A | | 8/1980 | Faso | 128/283 |
| 4,265,244 A | | 5/1981 | Hill | 128/283 |
| 4,368,737 A | * | 1/1983 | Ash | 604/175 |
| 4,553,271 A | * | 11/1985 | Baker | 623/14 |
| 4,695,273 A | * | 9/1987 | Brown | 604/173 |
| 5,041,102 A | * | 8/1991 | Steer et al. | 604/338 |
| 5,085,646 A | | 2/1992 | Svenson et al. | 604/175 |
| 5,098,398 A | | 3/1992 | Lundgren | 604/175 |
| 5,098,420 A | * | 3/1992 | Iacone | 604/338 |
| 5,257,975 A | * | 11/1993 | Foshee | 604/105 |
| 5,540,648 A | * | 7/1996 | Yoon | 600/114 |
| 5,591,145 A | | 1/1997 | Sachse | 604/349 |
| 5,647,861 A | * | 7/1997 | Steer et al. | 604/342 |
| 5,741,234 A | * | 4/1998 | Aboul-Hosn | 604/174 |
| 5,830,200 A | * | 11/1998 | Steer et al. | 604/338 |
| 5,947,941 A | * | 9/1999 | Leise, Jr. et al. | 604/338 |
| 6,210,384 B1 | * | 4/2001 | Cline | 604/338 |
| 6,254,642 B1 | * | 7/2001 | Taylor | 623/23.64 |

FOREIGN PATENT DOCUMENTS

| | | |
|---|---|---|
| EP | 0 592 131 A1 | 4/1994 |
| WO | WO 98/58691 | 6/1998 |

* cited by examiner

*Primary Examiner*—Sharon Kennedy
(74) *Attorney, Agent, or Firm*—Winston & Strawn LLP (57) ABSTRACT

An implant for implantation into an animal or a human body, that includes an axial interior section for fixation inside the body and an axial exterior section, extending outwards from the body for mounting of a device which can be detachably connected to the body via the ring. The interior section and the exterior section are connected to each other by at least one connecting section with at least one transverse opening. Through the transverse openings, tissue can be formed for fastening of the implant. The fastening can be additionally secured by placing a number of anchoring members in the transverse openings.

17 Claims, 9 Drawing Sheets

IMPLANT

CROSS-REFERENCE TO RELATED APPLICATIONS

This application is a continuation of the U.S. national phase designation of International Application PCT/DK00/00394 filed Jul. 12, 2000, the content of which is expressly incorporated herein by reference thereto.

BACKGROUND ART

The invention relates to an implant for implantation into an animal or a human body, comprising an axial inner portion for fixation inside the body and an axial outer portion extending outward from the body and serving for mounting of a device which can be detachably connected to the body via the ring.

There are numerous medical conditions in the gastrointestinal canal and in the urinary system which require a surgical intervention with temporary or permanent performance of a stoma. After such intervention, excrements or urine is traditionally collected in a stoma pouch, adhering to the skin and surrounding the stoma.

The demands for a tight adhesive surface are high. If liquid secretion penetrates the adhesive surface, this surface will loosen more or less, resulting in leakage from the pouch and release of an unpleasant smell.

Consequently, there is a demand for alternatives to traditional combinations of adhesive face plates and stoma pouches.

U.S. Pat. Nos. 4,265,244, 4,532,761 and 5,242,415 disclose partially biocompatible implants which form a leak-proof fastening device for the stoma pouch after ostomy surgery. These implants all comprise a flange portion to form a fixed anchor for the implant in the body. The flange can be wholly or partly covered with a biocompatible mesh that enables and encourages tissue repair and ingrowth of the implant.

To enable implantation of a device with such a flange, it is necessary to make a relatively large incision in the abdominal wall for insertion of the implant. The construction of such implants being relatively large and rigid, the surgically treated patient frequently senses the presence of the implant which causes discomfort.

GB 2 019 219 discloses yet another implant with a rigid flange, extending horizontally from the conical body. The flange is perforated by a number of holes to facilitate growth therethrough of fresh tissue, thereby improving tissue bonding between implant and body. This construction is large in width as well and consequently requires a large surgical incision, and the presence of the flange causes considerable discomfort for the patient.

Many of the above disadvantages have been rectified by the implant known from international patent application PCT/EP98/04029, where the inventors of the present invention are co-inventors. There still remains a need for additional devices that can provide improved performance.

SUMMARY OF THE INVENTION

The present invention provides an implant of the kind mentioned above, which implant requires a smaller surgical incision than known so far with no direct mucocutaneous contact and which can be safely and securely affixed to an underlying skin layer or into a muscle without being fitted with a flange.

The invention also provides an implant which is not sensed by the patient after implantation, and which can be detachably attached to and/or disconnected from devices such as, e.g., caps or pouches, thereby giving the surgically treated patient unprecedented comfort.

The invention further provides an implant that causes an unprecedented minimum of allergic and inflammatory reactions.

In addition, the invention provides an implant that has an easily adjustable axial extension to fit heavy as well as thin patients.

The novel and unique features of the invention are based on the fact that in principle the implant has a generally tubular form, with an interior section comprising an anchoring ring and a continuous connecting section between this ring and an exterior section. The exterior section has at least one throughgoing transverse opening.

When the connecting section of the interior section is a rod extending between the anchoring ring and the exterior section, a single opening is produced between them. When the connecting section of the interior section is more than one rod extending between the anchoring ring and the exterior section, the connecting section is constructed as an open grid. Particularly appropriately, the rods may be evenly distributed along the anchoring ring and the exterior section.

When in this way at least one throughgoing transverse opening is produced between the interior section and the exterior section of the ring, new healed tissue and vascular systems can naturally form through such transverse opening (s) in such a way that in the course of very short time, a natural blood supplied biological fastening of the implant to the body will be established with, in the course of implantation, the implant being at least partly embedded into the body.

The total quantity of non-biological material embedded into the body and in direct contact with body tissue will be considerably smaller than that provided by other known devices so far. The risk and the probability of allergic and inflammatory reactions have therefore been reduced significantly in a simple way and are far smaller than when previously established devices are used.

A part of the axial extension of the at least one throughgoing transverse opening may in some cases advantageously be left outside the body, allowing ingrowth through the at least one transverse opening to occur partly on the outside and over cutis. In this way, only an insignificant part of the implant is implanted, while at the same time a strong fixation is secured.

At the end facing the connection section, the exterior section of the implant can advantageously be fitted with a ring-shaped section with a number of evenly distributed suturing perforations. By securing the implant solidly in a skin layer by suture through the suturing perforations in the first phase after surgery, the implant can be fixated at the required site in a simple manner. Thus, when the implant has been made resistant to compressive and tensile stress in this way, optimal conditions have been procured for the subsequent tissue healing phase, where fresh tissue grows through the transverse opening(s).

By, e.g., producing several rings of suturing perforations, a possibility of leaving a larger or smaller part of the implant outside the body is created. In this way, suturing can be performed either in cutis or in subcutis or in both skin layers, depending on how much of the exterior section of the implant is desired to remain outside the body.

In a second embodiment of the invention, the end opposite the exterior section of at least one of the rods of the connecting section tapers. When each rod tapers towards the free end, the implant can slidably be inserted readily through the skin around, e.g., a stoma using a very simple implantation method, and subsequently it can slidably be inserted further down towards an underlying muscle or fascia.

In an alternative implantation method, a number of insertion apertures corresponding to the number of rods can be made in the abdominal wall, serving to accommodate the rods.

Marking of insertion apertures can be made either by simple sketching and making them one at a time, or by simultaneous marking of all apertures by a purpose-designed cutting former plate for making an aperture for each rod at one time. In this way, the depths and widths of all apertures are ensured in a simple way for accurate accommodation of the rods to the necessary extent.

At least one throughgoing hole can be made at the free end of each rod, with the hole being arranged for accommodating at least part of the anchoring ring. When an anchoring ring of a material which is the same as or similar to, e.g., the implant is led through the holes of the rods, fastening between implant and body will become exceptionally strong. Consequently, the implant becomes immediately resistant to compressive and tensile stress, and the anchoring ring locks the implant in the tissue layer, where placement of the rods is chosen and through which the anchoring ring is forced.

When the ring is slidably inserted through the holes in the rod, the ring, the interior section and the rods together form transverse openings, corresponding to the previously mentioned transverse openings, in which subsequent appropriate attachment of a number of anchoring means is enabled. Similarly, a space between anchoring means and transverse openings can, as described above, be provided by means of antimicrobial impregnated threads.

This embodiment of the implant provides an extremely strong fastening in the tissue, and the implantation only requires a very small surgical intervention. If removal of the implant may be required at a later stage, this can be done in a simple way by removal of the ring fixating the implant first and subsequent removal of tissue formation at the suturing perforations, if any, whereupon the implant can be pulled out in a simple manner.

BRIEF DESCRIPTION OF THE DRAWINGS

The invention is described in more detail below, describing exclusively examples of embodiments with reference to the drawing, in which.

DETAILED DESCRIPTION OF PREFERRED EMBODIMENTS

For patients with e.g. particularly pronounced obesity, the axial extension of the implant must be sufficiently long for the anchoring ring to bear against a biological platform such as a muscle. The above mentioned embodiment is particularly applicable for such patients, as the rods in such cases may advantageously be designed with additional length In as much as different patients have different thicknesses of skin and fat layers as well as a more or less deep-set musculature, the axial extension of the implant is adjustable in the alternative embodiments of the implant according to the invention. Consequently, the axial extension is advantageously adaptable to the actual individual need, required in the immediate situation.

In the above described embodiments of the implant according to the invention, the connecting section is a straight rod, connecting the anchoring ring and the exterior section in principle at right angles.

In an alternative embodiment, the connecting section can consist of at least one rod, extending in waveform between the anchoring ring and the exterior section.

For a particularly corpulent or adipose patient, the at least one rod can advantageously be U-shaped, V-shaped or S-shaped, in principle following the curve of the ring.

After evaluation of the condition of the individual patient and estimation of a necessary axial extension of the implant, the exterior and interior sections of the implant are pressed against each other to reduce the axial extension of the implant, or the exterior and interior sections of the implant are pulled in opposite directions to increase the axial extension of the implant, causing the axial extension of the implant to subsequently match the actual patient and the immediate situation accurately.

Other geometrical configurations for the connecting section, e.g. zigzag configurations of linked U's, V's or S's, or e.g. sine or cosine curves, are also included within the scope of this invention.

In a second alternative embodiment, which is particularly advantageous for e.g. obese patients, the at least one rod extends between the anchoring ring and the exterior section along an in principle helical shape.

Such a construction provides high flexibility of the axial extension of the implant, and larger and smaller extensions are obtainable in a manner similar to that of the above mentioned embodiment, where V-shaped rods form the connecting section, namely by pulling the interior and exterior sections in opposite directions or by pressing the interior and exterior sections together, respectively. By giving the connecting section a helical shape with several threads, the axial extension can be much increased.

Production of threads in such a helix is particularly simple by merely cutting up a connecting section, which is a connecting part between interior and exterior sections, until the required number of threads has been produced.

A particularly solid construction is achieved, when the connecting section consists of several parallel helixes, where the space between the threads produces one or several openings, forming the previously described transverse openings.

By giving the connecting part a helical shape, the flexibility of the axial extension is high, with no requirement for implantation of additional non-biological material for providing a means for fixation of the implant to a biological platform.

The width or the thickness of the rod is variable, depending on the requirements for stability and flexibility of a device.

By turning the anchoring ring and the exterior section of the implant on their common axis in opposite directions, it is possible to increase or reduce the diameter of part of the connecting section compared to the diameter of the exterior section and the anchoring ring.

To additionally ensure fastening in the body, anchoring means can be affixed to the anchoring ring with mutual angle spacing. The anchoring means extend outwards to a free end and can advantageously consist of a biocompatible, flexible material.

By way of example, the anchoring means can be porous, flexible, elongated textile meshes, produced in a well-known biocompatible material.

Examples of such applicable polymers are DACRON, PROLENE, VICRYL, GORE-TEX or SURGIPRO.

By producing the anchoring means of textiles, they become so flexible that they advantageously can be directed in any fixation direction. The length of the anchoring means is adjustable after the individual anatomical conditions, and their ductility and flexibility enable fixation of the anchoring means to e.g. more or less deep-set muscularis or fascia and at different angles and spaces from the interior section.

Application of anchoring means for fixation of the implant will contribute to advantageously reduce the greatest required axial extension of the ring, and to advantageously reduce the quantity of implanted non-biological material correspondingly.

To prevent that the anchoring means act as wicks for bacteria-rich secretion from the excrements, each anchoring means can be spaced apart from the relevant transverse opening by means of threads of a biocompatible material.

By impregnating the threads with an anti-microbial preparation, e.g. $AgNO_3$ or an antibiotic composition, the risk of post-operative abdominal infection is very small or has been entirely eliminated.

In case of patients with e.g. obesity, hernia, or cicatricial tissue formation, or patients developing such post-operative or similar discomforts at a later stage, it may be required at least temporarily to enlarge the axial extension of the exterior section to permit and/or facilitate mounting of the device which will be attached to the exterior section.

Similarly, for a period after an operation where an implant has been implanted in a patient, oedema and swelling in the operated tissue may occur which will hinder correct attachment of e.g. a stoma pouch on the implant.

Such disadvantages can be eliminated in a simple way, when the implant comprises an extension ring which in use can be mounted in such a way that the part of the axial extension of the implant comprising the exterior section can be advantageously increased. The extension ring has a connecting portion which can be detachably connected to the exterior section, and facing in the opposite direction of the connecting portion, one free end part which can be mounted with a detachable device desired connected to the body.

By fitting the connecting portion of the extension ring with a number of catches, in mounted state of the connecting portion detachably locking under a flange on the exterior section, the extension ring can in a simple way be attached to either the implant or to an additional extension ring.

Optimum assembly of the extension ring is ensured when the edge of the connecting portion facing the exterior section of the implant in mounted state is designed with a circumferential groove with a bottom designed to bear closely against the adjacent edge of the flange of the exterior section.

In addition, by interposing an O-ring between the bottom of the circumferential groove of the connecting portion and the adjacent edge of the flange of the exterior section, completely tight sealing between the extension ring and the implant is secured.

The inside diameter of the extension ring corresponds to the inside diameter of the implant, and when mounted on the implant, an entirely plane transition between the extension ring and the implant is provided.

To prevent accidental pulling of the extension ring off the implant, e.g., when a device is attached or removed, the extension ring and the implant can also be interlocked by a locking ring passing closely over the extension ring. Such a locking is most expediently achieved by designing the locking ring with at least one radial interior portion that is equivalent to or slightly greater in diameter than the space between the exterior of two of the diametrically opposite catches of the connecting portion.

When the radial interior portion is shaped as a circumferential groove for accommodating the catches of the connecting portion, the joint between the implant and the extension ring can be fixated and sealed in a simple way.

The implant with belonging parts can advantageously be manufactured of a material which is known not to produce allergic reactions and which is approved by the health authorities for application in implantations.

A preferably rigid implant can be manufactured of titanium or possibly of a titanium alloy.

A preferably bendable and flexible implant can be manufactured of a biocompatible synthetic or biosynthetic polymer. As an example, polyurethane or polyurethancopolymer can be mentioned. Furthermore, at least part of the implant can advantageously be covered with such biocompatible polymer.

The implant according to the invention can advantageously be applied in enterostomies. Enterostomies are accomplished by exteriorizing the intestine through an opening in the abdominal wall. The intestinal opening is sutured to the skin in the course of the process in such a way that skin and intestine will subsequently grow together. The implant can be implanted prior to performance of a stoma or after conclusion of such, thus surrounding the stoma in a distance to prevent direct mucocutaneous contact.

Alternatively, the implant can be implanted and sutured to the intestine as well as to epidermis via the suturing perforations.

The implant according to the invention can be designed with any combination of diameter and axial extension and is consequently applicable together with any shape, size or type of performed ostomy, e.g., colostomy, ileostomy, urostomy, pneumostomy or tracheotomy.

Alternatively, the implant can advantageously be applied in cases where a device is required to be attached to the body. Such a device in form of a stoma pouch is known from the applicants' Danish patent application PA 2000 00025.

As an additional example can be mentioned a very thin, flexible implant, relatively great in diameter. Such an implant can be implanted into a bald top of the head, and a wig designed to be detachably linked to the implant can thus be attached to and removed from the implant in a simple way, thus ensuring wig wearers that their wigs are firmly fixated under all circumstances and external influences.

Figure 1:
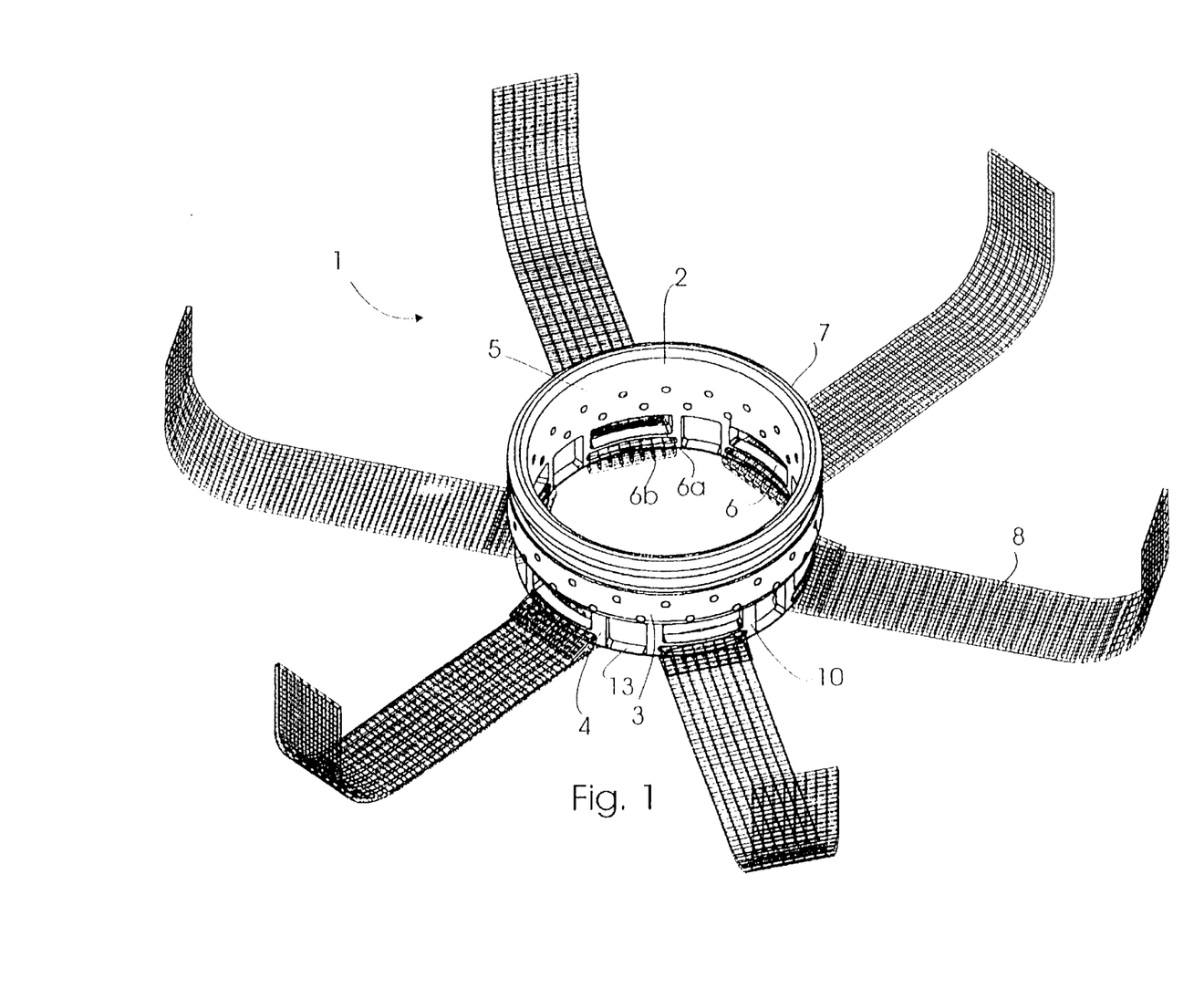
FIG. 1 shows, in perspective, a first embodiment of an implant with anchoring means according the invention.
Figure 2:
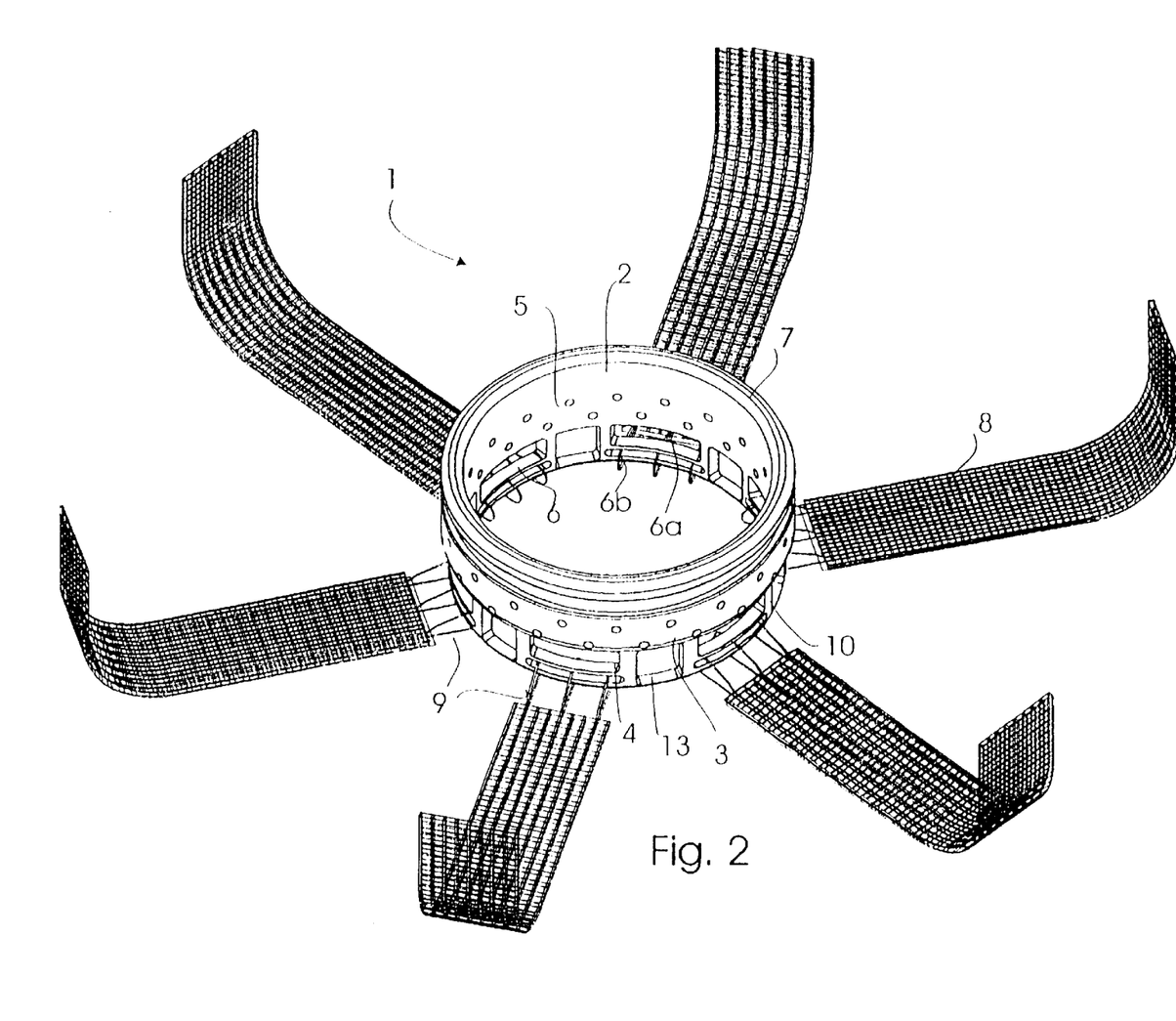
FIG. 2 shows the same, but with anchoring means spaced apart from the implant by means of threads.

The implant shown in FIGS. 1 and 2 is in its entirety designated with reference number 1.

FIGS. 1 and 2 show an implant 1 with an axial exterior section 2, an axial interior section 3, consisting of an anchoring ring 13 and a continuous connecting section 4 between the anchoring ring 13 and the exterior section 2. In the part of the exterior section 2 facing the connecting section 4, one or several rings of suturing perforations 5 are designed, and the anchoring ring 13 and the exterior section 2 are in the shown example connected by a connecting section with twelve rods 10, forming twelve transverse openings 6, that in the embodiment of FIGS. 1 and 2 as an example each are divided into two fractional transverse openings 6a and 6b. In FIGS. 1 and 2 the implant is as an example shown with six transverse openings 6, but this embodiment of the implant may contain any number of transverse openings 6 within the scope of the invention.

The exterior section 2 is designed with a flange 7, to which by way of example a stoma pouch or a locking device (not shown) can be attached. Anchoring means 8 are mounted in the fractional transverse openings 6b and in the illustration example all six fractional transverse openings 6b are fitted with anchoring means 8. The anchoring means 8 are preferably manufactured of a porous biocompatible polymer and are flexible. The anchoring means 8 are here shown with equivalent lengths, but can within the scope of the invention be longer or shorter.

In FIG. 2, the anchoring means 8 are distanced from the transverse openings 6b by means of threads 9, which are preferably impregnated with an antimicrobial preparation.

Figure 3:
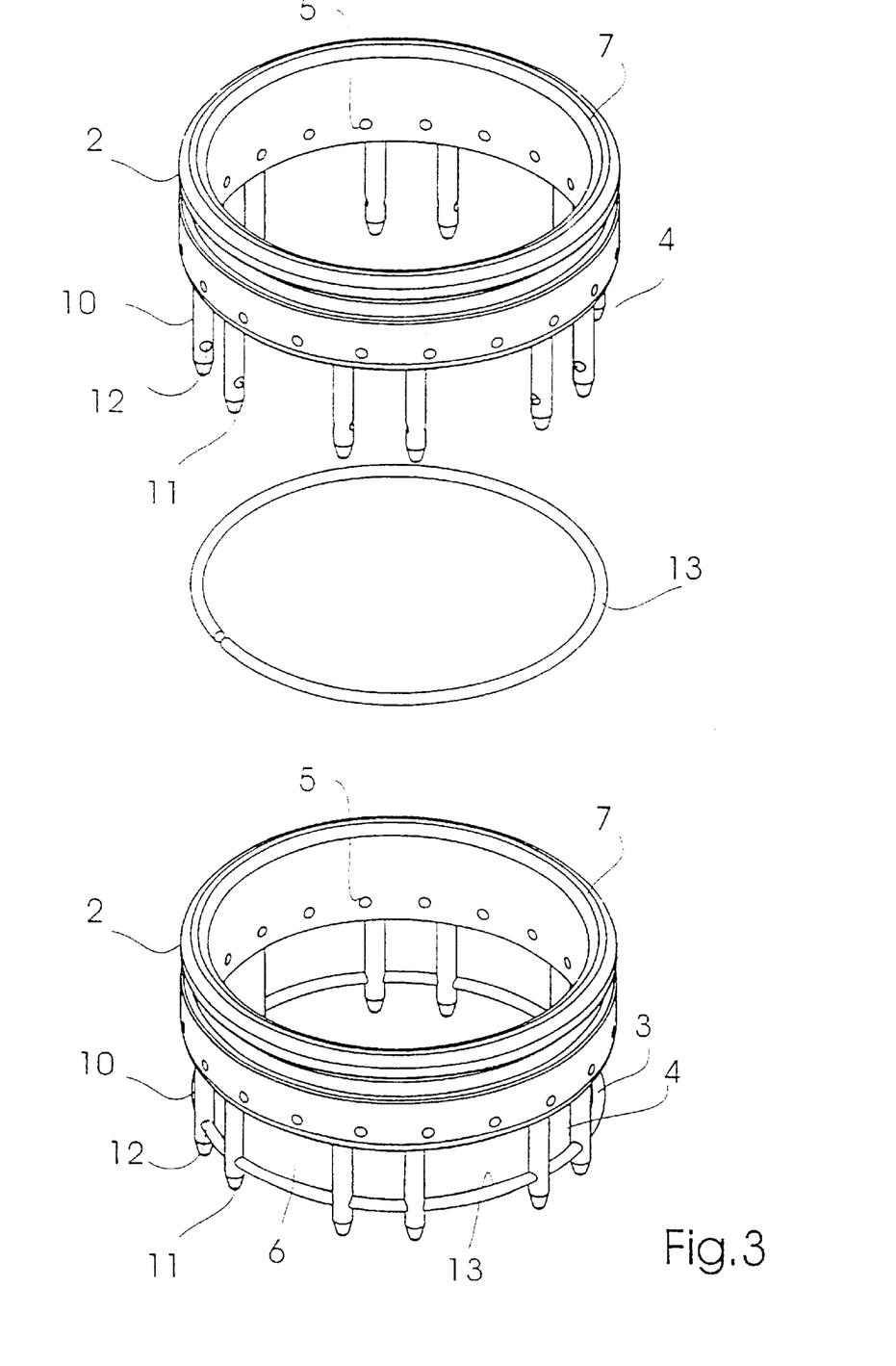
FIG. 3 shows, in perspective, an exploded view of a second embodiment of an implant according to the invention.

FIG. 3 shows a second embodiment of the implant according to the invention. The exterior section 2 with the flange 7 has in the shown example only one ring of suturing perforations 5 and along the part of the circumference of the exterior section 2 facing in the opposite direction to the flange 7, twelve evenly distributed, elongated, axially extending rods 10 are mounted, forming the connecting section 4. Each rod 10 tapers towards the free end 11. In the free end 11 of each rod 10 at least one hole 12 is made, through which an anchoring ring 13 can be inserted.

In the transverse openings 6, which are produced by inserting the anchoring ring 13 into the holes 12 of the rods 10, anchoring means 8 (not shown) can be placed in a similar manner as shown in FIG. 1 or 2.

The implants shown in FIGS. 1, 2 and 3 are mainly ring-shaped with a relatively small axial extension.

The embodiments of the implant according to the invention shown in FIGS. 4–9 are alternative embodiments of the shown implant of FIGS. 1 and 2. However, the embodiments of FIGS. 4–9 are all adjustable to a larger axial extension, and identical parts are referred to with identical reference numbers.

Figure 4:
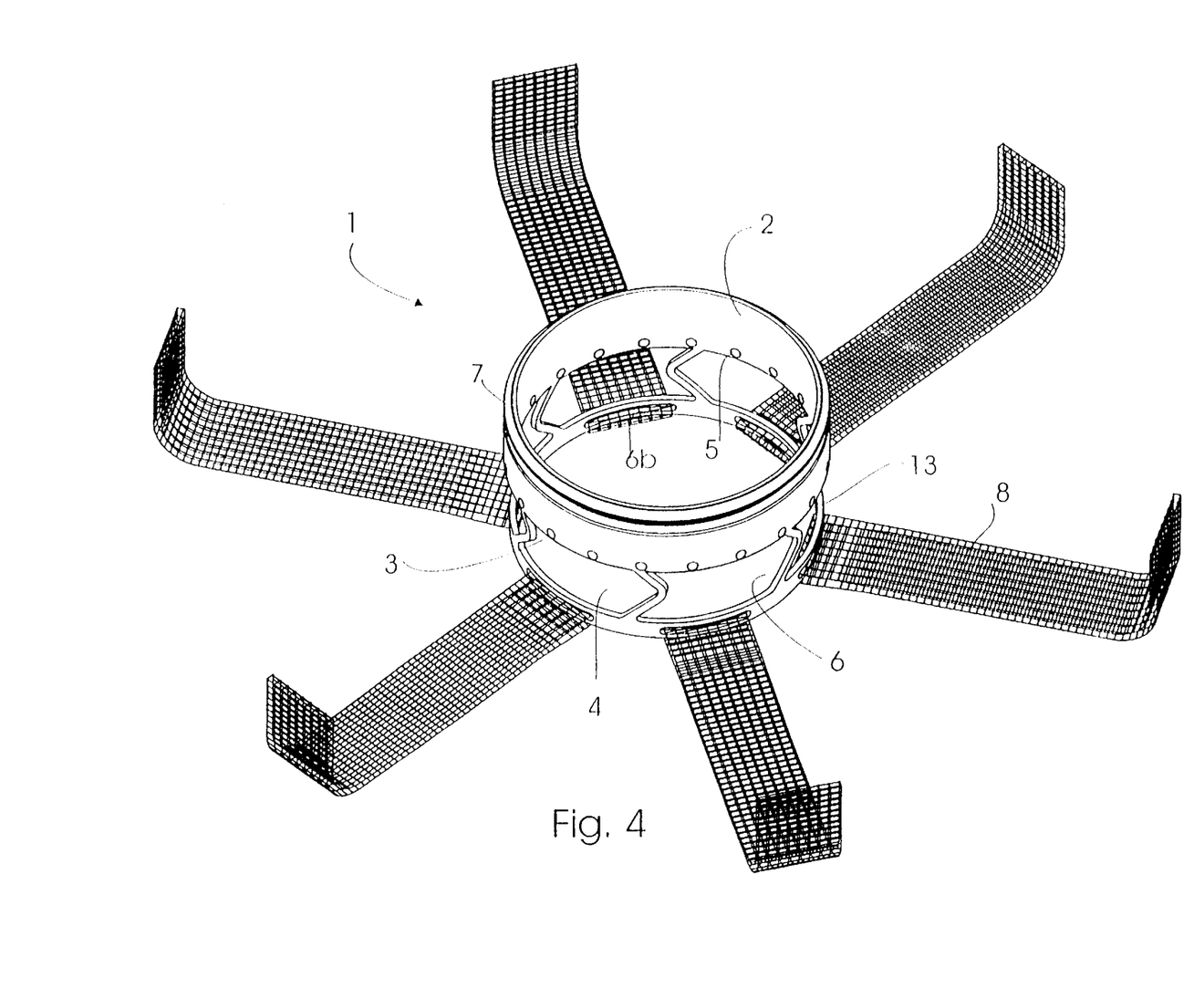
FIG. 4 shows, in perspective, a third embodiment of an implant according to the invention.

The embodiment shown in FIG. 4 has a connecting section 4, as an example consisting of six rods 10, forming six transverse openings 6. The rods 10 are in the shown example of embodiment bent into a V-shape, but may within the scope of the invention be given any shape. As an example can be mentioned an S-shape, a U-shape or coherent combinations of such shapes, e.g. a zigzag-shape. In addition, the bent rod 10 is bent mainly to follow the tubular shape of the implant. By pulling the exterior section 2 away from the anchoring ring 13, the angle between the legs of the V is enlarged, and the axial extension of the implant can be increased to a maximum where the space between the interior section and the exterior section corresponds to the total of the length of the two legs of the V. Six anchoring means 8 are attached to six evenly distributed fractional transverse openings 6b.

Figure 5:
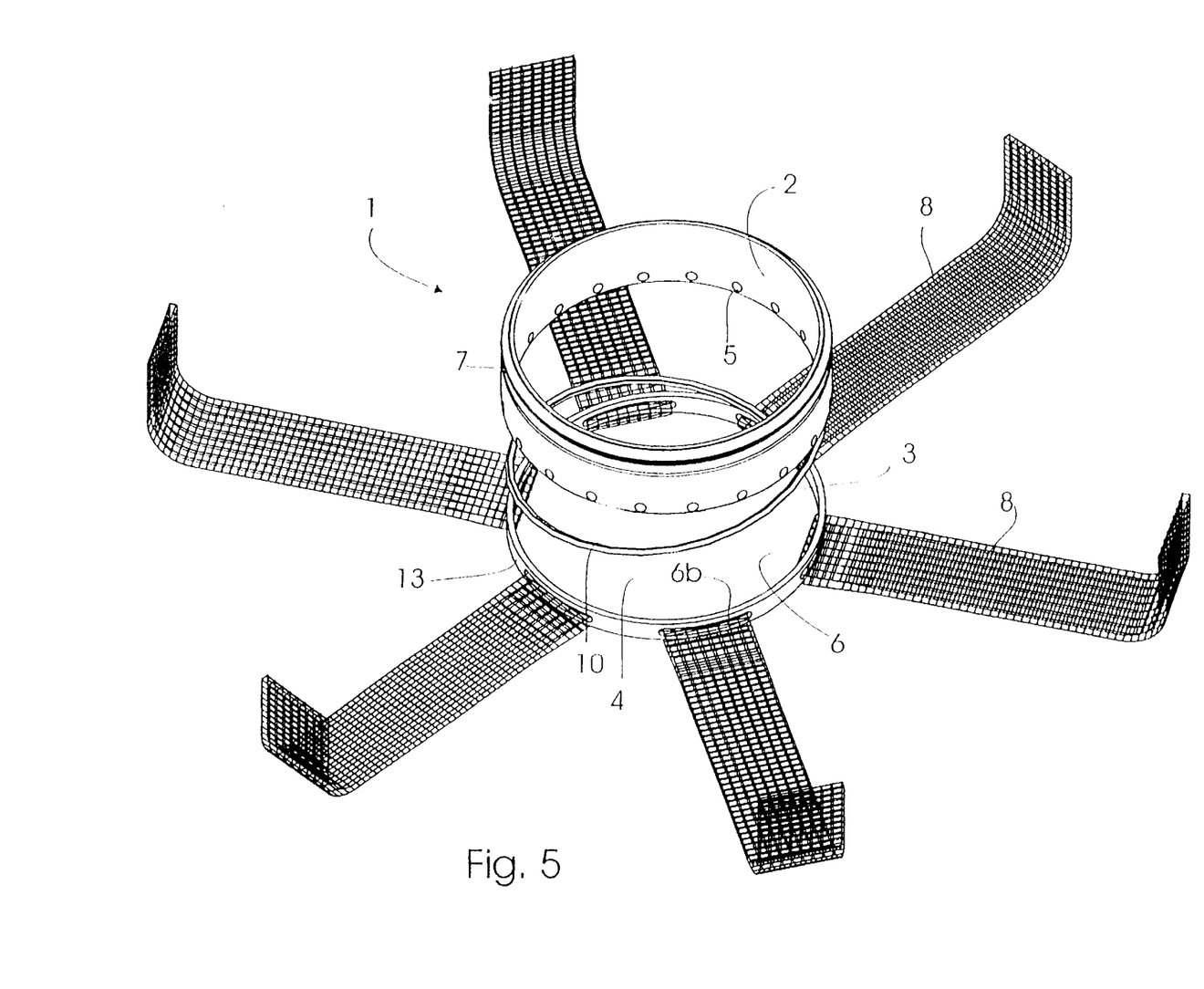
FIG. 5 shows, in perspective, a fourth embodiment of an implant according to the invention.

In the embodiment of FIG. 5, the interior section 3 and the exterior section 2 are connected by the connecting section 4, consisting of one helical rod 10. The connecting section 4 is here shown as a narrow thread, but the invention is not limited to narrow threads in as much as wide threads may be more suitable for some purposes where the demands for a highly stable construction with great axial extension are heavy.

Figure 6:
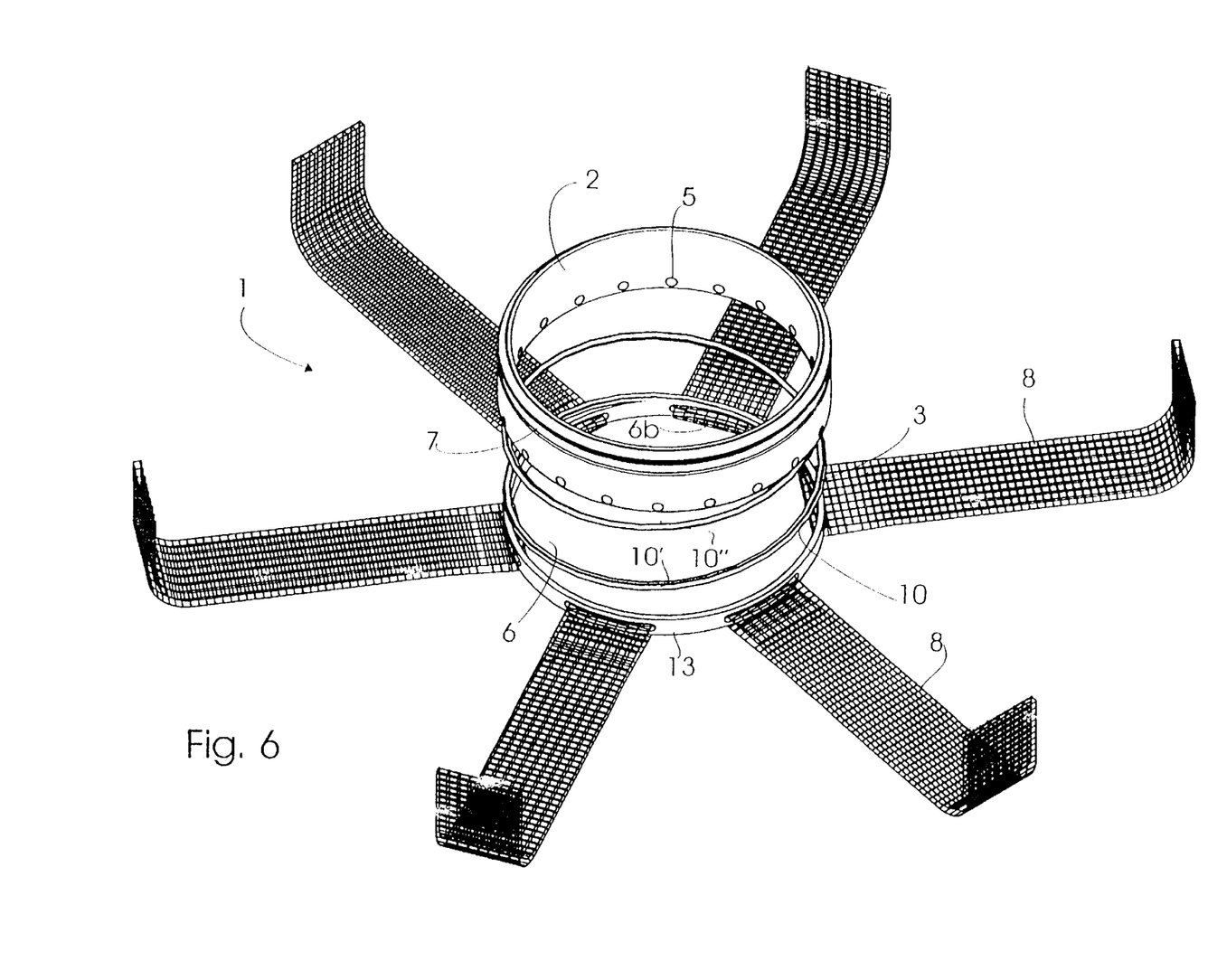
FIG. 6 shows, in perspective, the fourth embodiment, but with two threads on the connecting section.

The embodiment of FIG. 6 corresponds to the embodiment shown in FIG. 5, but the helical connecting section 4 has in this case a rod 10 with two threads 10' and 10".

Figure 7:
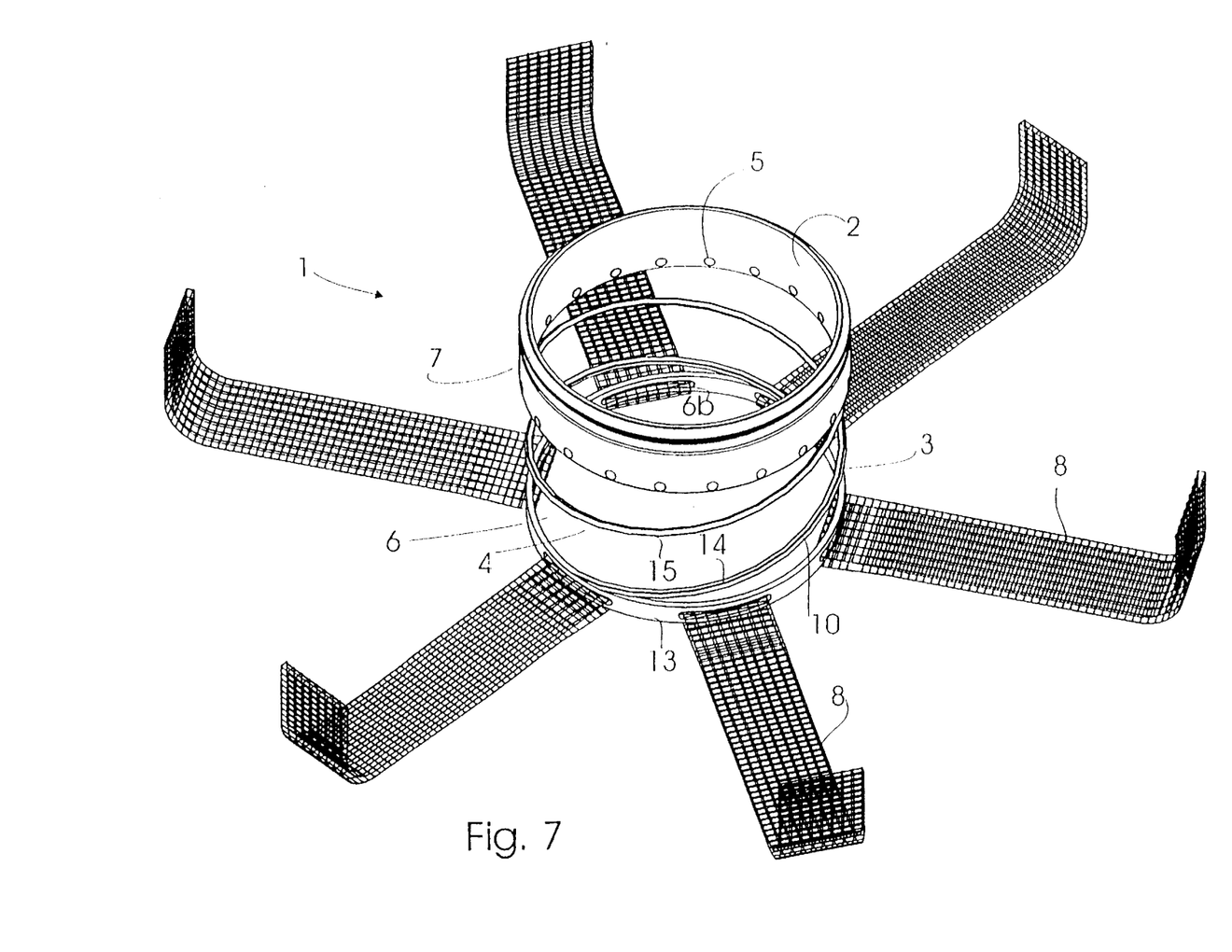
FIG. 7 shows, in perspective, the fourth embodiment, but with two rods on the connecting section.

The embodiment shown in FIG. 7 has a connecting section 4, consisting of two rods 10 each in the shown example with a helix with a thread 14 and a thread 15 respectively, extending from two spots on the anchoring ring 13, diametrically opposite one another. This construction is very stable and provides a well-defined passage for a body part, e.g. a vessel or part of an intestine, to be exteriorized through the implant 1. As in the above shown embodiments, fresh healed tissue and vascular system will be formed in a natural way through the transverse openings 6, enabling establishment of a natural blood supplied biological fastening of the implant in the course of very short time.

Figure 8:
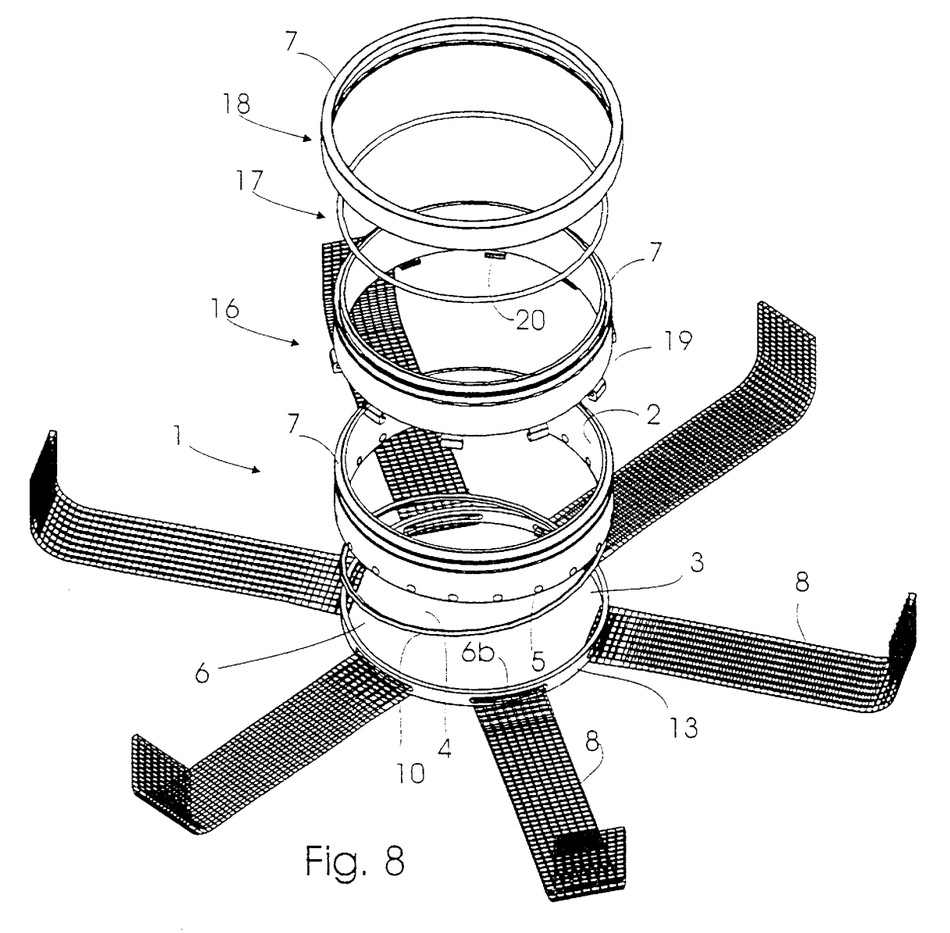
FIG. 8 shows, in perspective and partly sectional, an exploded view of an implant with an extension ring, an O-ring and a locking ring.

FIG. 8. shows an implant 1, similar to the implant shown in FIG. 5, an extension ring 16, an)-ring 17 and a locking ring 18. The extension ring 16 has a connecting portion 19 with catches 20 and a flange 7, identical to the flange 7 of the implant 1 and placed opposite the connecting portion 19.

Figures 9, 9A:
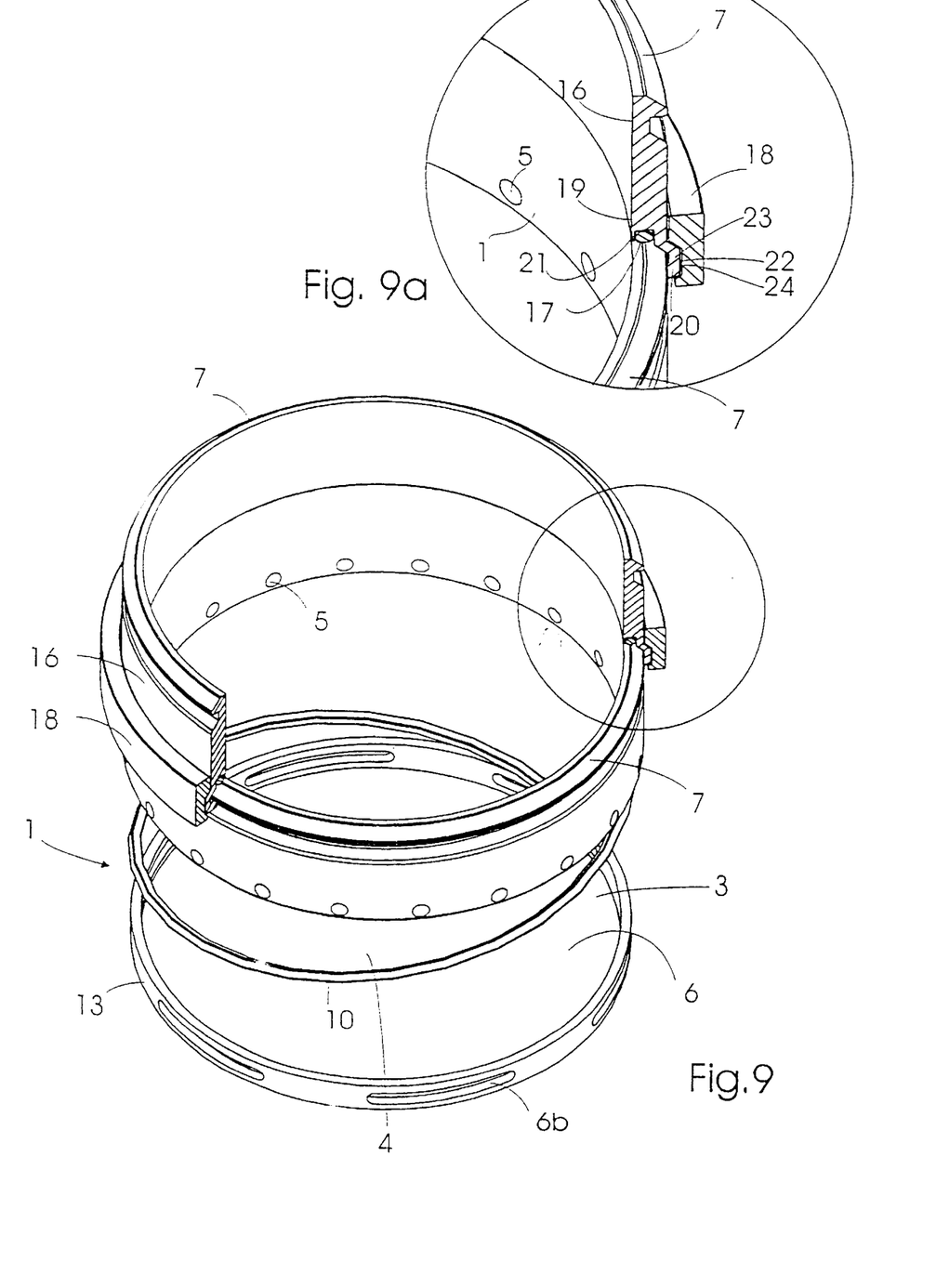
FIG. 9 shows, in perspective and partly sectional, the extension ring in mounted state on an implant, where it is locked by a locking ring.
FIG. 9a shows on an enlarged scale a feature of FIG. 9.

The coupling of the extension ring 16 to the implant 1 is shown in more detail in FIGS. 9 and 9a. In FIG. 9 the extension ring 16 is attached to the implant 1 and locked by the locking ring 18. Detail FIG. 9a shows sectional and in more detail the coupling of the implant 1 to the extension ring 16 and the locking by means of the locking ring 18.

The extension ring 16 is shown in mounted state on the implant 1, where the catches 20 of the extension ring lock under a flange 7 on the exterior section 2 of the implant 1.

The edge of the connecting portion 19, in mounted state facing the exterior section 2 of the implant, has a circumferential groove 21, the bottom of which bears closely against the adjacent edge of the flange 7 of the exterior section 2.

To ensure tight sealing of the extension ring 16 to the implant 1, an O-ring 17 has been affixed between the bottom of the circumferential groove 21 of the connecting portion 19 and the adjacent edge of the flange 7 of the exterior section 2.

The locking ring 18 has a radial interior portion 23 in diameter corresponding to the space between the exterior sections 24 of diametrically opposite catches 20 on the connecting portion 19 of the extension ring 16. The radial portion 23 of the locking ring 18 has a circumferential groove 22, which is slidably inserted over the catches 20 of the extension ring 16. In mounted state, the locking ring presses the extension ring 16 firmly and tightly sealing against the implant 1.

Additional extension rings can be mounted above one another until appropriate necessary extension has been obtained.

EXAMPLES

Example 1

Various combinations of the implant have been tested, i.e., both with and without a biocompatible polymer cover, and implants of various materials have been applied, all of which are within the scope of this invention.

Approval for the tests has been procured and granted by the Dyreforsøgstilsynet (Danish Animal Experiment Authorities), Slotsholmsgade 12, st., 1216 Copenhagen K, Denmark, to prepare for implantation into 10 pigs per year under general anaesthesia.

Specially bred Güttingen test pigs were observed for up to 2 months in stalls prior to surgery in consideration of existing rules for animal experiments and after conclusion of colostomy and intracutaneous implantation of the implant, the pigs were treated with analgesics, if necessary.

The animals were killed after a period of up to 31 days, and the implant and the adjacent tissue were examined histologically at Biomedical Laboratory, Odense University Hospital, Denmark.

The results are compiled in the below table, which demonstrates:
that none of the pigs showed signs of allergic reaction; and
a very high degree of ingrowth through the transverse openings as well as through the meshes was observed, resulting in a very high degree of intradermal fixation, providing a means for a detachable link to the body via the ring.

The histological studies were performed on colon inclusive of a circular piece of the skin surrounding the stoma. The results are shown in the below table.

However, pigs are less suitable for this type of experiment, having a relatively high tendency towards developing stenosis and fibrosis.

Example 2

Performance of Human Sigmoidestomy

Approach is created through umbiculus, the sigmoideum snare is released by incising fascia fusion layer of Toldt. A marked access site is prepared on the front abdominal wall, and the implant which has been kept in gentamycin solution is implanted and secured to the body by fixating the interior section of the implant to fascia and by tunnelling the PROLENE meshes and fixating them to fascia. New skin is adapted into the implant, which is secured by suture to the skin through the suturing perforations. This ensures that the implant is suitably fixated and well-placed. In the center of the implant a hole is formed in the abdominal wall. Through this hole sigmoid is exteriorized and left unfashioned and unfixated to begin with. After 12 days the intestine is cut off to a suitable level, and a pouch designed for attachment to the implant is mounted. The condition of the patient is good.

What is claimed is:

1. An implant for implantation into an animal or human body, comprising: an axial interior section for fixation inside the body, said interior section comprising an anchoring ring, and an axial exterior section extending outwards from the body and serving for mounting of a device which can be detachably connected to the body via the implant, wherein

|   | Implant | Number of implantation days | Rejection | Fibrotic | Ingrowth/ Attachment | Infection | Eosino- philocytes | Cause of destruction |
|---|---|---|---|---|---|---|---|---|
| 1 | Implant (covered with GORE-TEX, and PROLENE meshes applied) | 18 | 0 | + | 0 | 0 | 0 | Intestinal stenosis |
| 2 | Implant | 28 | 0 | + | 0 | 0 | 0 | Poor general condition |
| 3 | Implant (covered with GORE-TEX, and PROLENE meshes applied) | 7 | 0 | + | 0 | 0 | 0 | Intestinal stenosis |
| 4 | Implant | 31 | 0 | + | 0 | 0 | 0 | Not registrered |
| 5 | No implant | 8 | Necrosis of stoma | + | Not registrered | (+) | 0 | Poor general condition/hernia |
| 6 | No implant | 30 | Necrosis of stoma | + | Not registrered | 0 | 0 | Intestinal stenosis |
| 7 | Implant (covered with GORE-TEX, and GORE-TEX meshes applied) | 30 | Stenosis | + | 0 | 0 | 0 | Stenosis/ no appetite |
| 8 | Implant | 7 |  | + | 0 | Fibrinoid peritonitis | 0 | No appetite/ poor general condition |
| 9 | Implant (skin-skin) | 14 | 0 | + | Ingrowth of cutis through transverse openings of implant | 0 | 0 | Not registrered | the interior section further comprises a connecting section extending between the anchoring ring and the exterior section, said connecting section including at least one rod providing at least one throughgoing transverse opening in the connecting section.

2. An implant according to claim 1, wherein the connecting section includes a number of rods extending between the anchoring ring and the exterior section, said number of rods are together forming an open grid.

3. An implant according to claim 2, wherein the end part of at least one of the rods facing in the opposite direction of the exterior section of the connecting section is tapered and that in each rod is formed a throughgoing hole designed for accommodating at least a part of the anchoring ring.

4. An implant for implantation into an animal or human body, comprising: an axial interior section for fixation inside the body, said interior section comprising an anchoring ring, and an axial exterior section extending outwards from the body and serving for mounting of a device which can be detachably connected to the body via the implant, wherein the interior section further comprises a connecting section extending between the anchoring ring and the exterior section, said connecting section including at least one rod providing at least one throughgoing transverse opening in the connecting section, wherein the connecting section includes at least one rod extending in waveform between the anchoring ring and the exterior section.

5. An implant according to claim 4, wherein the shape of the at least one rod is a U, a V or an S.

6. An implant according to claim 1, wherein the connecting section includes at least one rod that extends along a helix between the anchoring ring and the exterior section.

7. An implant according to claim 1, wherein the implant comprises a number of elongated anchoring means affixed to the anchoring ring with mutual angular distance and extending from the anchoring ring to a free end, and that the anchoring means comprises a biocompatible, flexible material.

8. An implant according to claim 7, wherein the part of each anchoring means closest to the anchoring ring includes at least one thread affixed to the anchoring ring and extending in the longitudinal direction of the anchoring means, and that the at least one thread comprises a biocompatible material.

9. An implant according to claim 8, wherein at least one thread of each anchoring means is impregnated with an antimicrobial preparation.

10. An implant according to claim 9, wherein the antimicrobial preparation is $AgNO_3$ or an antibiotic composition.

11. An implant for implantation into an animal or human body, comprising: an axial interior section for fixation inside the body, said interior section comprising an anchoring ring, and an axial exterior section extending outwards from the body and serving for mounting of a device which can be detachably connected to the body via the implant, wherein the interior section further comprises a connecting section extending between the anchoring ring and the exterior section, said connecting section including at least one rod providing at least one throughgoing transverse opening in the connecting section, wherein the implant further comprises an extension ring which has a connecting portion for detachably connecting the extension ring to the exterior section and a free end part facing opposite the connecting portion for detachably mounting a device for connecting to the body.

12. The implant according to claim 11, wherein the connecting portion of the extension ring includes a number of catches which in mounted condition of the connecting portion detachably lock under a flange on the exterior section.

13. An implant according to claim 11, wherein in the edge region of the connecting portion facing the exterior section of the implant in mounted state includes a circumferential groove having a bottom which closely abuts against an adjacent edge region of the flange of the exterior section.

14. An implant according to claim 13, wherein the implant comprises an O-ring inserted between the bottom of the circumferential groove of the connecting portion and the adjacent edge region of the flange of the exterior section.

15. An implant according to claim 1, wherein the connecting section has two diametrically opposite catches on its exterior and the implant comprises a locking ring having at least one radial interior portion which has a diameter equivalent to or slightly greater than the distance between the exterior sides of the catches of the connecting section.

16. An implant according to claim 15, wherein the said radial interior portion of the locking ring is designed as a circumferential groove.

17. An implant according to claim 1 having a generally tubular form.

* * * * *